US010602774B2

(12) United States Patent
Hawes et al.

(10) Patent No.: US 10,602,774 B2
(45) Date of Patent: *Mar. 31, 2020

(54) E-VAPOR DEVICES INCLUDING PRE-SEALED CARTRIDGES

(71) Applicant: Altria Client Services LLC, Richmond, VA (US)

(72) Inventors: Eric Hawes, Richmond, VA (US); Raymond Lau, Richmond, VA (US); Ben Sharp, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 46 days.

This patent is subject to a terminal disclaimer.

(21) Appl. No.: 14/998,040

(22) Filed: Apr. 22, 2015

(65) Prior Publication Data

US 2017/0202265 A1  Jul. 20, 2017

(51) Int. Cl.
*A24F 47/00* (2006.01)
*A61M 11/04* (2006.01)
*A61M 15/06* (2006.01)

(52) U.S. Cl.
CPC ............ *A24F 47/008* (2013.01); *A24F 47/00* (2013.01); *A24F 47/002* (2013.01);
(Continued)

(58) Field of Classification Search
CPC ...... A24F 47/008; A24F 47/00; A24F 47/002; A24F 47/004; A61M 11/041;
(Continued)

(56) References Cited

U.S. PATENT DOCUMENTS 5,269,327 A   12/1993  Counts et al.
6,053,176 A    4/2000  Adams et al.
(Continued)

FOREIGN PATENT DOCUMENTS

CA   2866283 A1   12/2014
CN   101986906 A   3/2011
(Continued)

OTHER PUBLICATIONS

International Search Report and Written Opinion dated Aug. 18, 2016 for corresponding International Application No. PCT/US2016/028039.
(Continued)

*Primary Examiner* — Michael J Felton
*Assistant Examiner* — Sonny V Nguyen
(74) *Attorney, Agent, or Firm* — Harness, Dickey & Pierce, P.L.C.

(57) ABSTRACT

An e-vapor device may include a cartridge configured to hold a vapor precursor therein. The e-vapor device may additionally include a dispensing body including a ratchet assembly and configured to receive a vaporizer to interact with the ratchet assembly. The vaporizer is configured to access the vapor precursor in the cartridge via a coupling action and to heat the vapor precursor to generate a vapor. The ratchet assembly is configured to undergo a mechanical incrementation with each coupling action to facilitate a simultaneous removal of the cartridge with the vaporizer coupled thereto after a designated number of coupling actions. Accordingly, the overuse of the vaporizer and the adverse sensory effects associated therewith can be reduced or prevented.

14 Claims, 12 Drawing Sheets

(52) U.S. Cl.
CPC ......... *A24F 47/004* (2013.01); *A61M 11/041* (2013.01); *A61M 11/042* (2014.02); *A61M 15/06* (2013.01)

(58) Field of Classification Search
CPC ................ A61M 11/042; A61M 15/06; A61M 2205/273; A61M 2205/27; G05G 5/12; G05G 5/18; G05G 5/24
USPC ............................ 131/182, 329, 330; 74/575
See application file for complete search history.

(56) References Cited

U.S. PATENT DOCUMENTS

| | | | |
|---|---|---|---|
| 8,757,169 | B2 | 6/2014 | Gysland |
| 8,851,068 | B2 | 10/2014 | Cohen et al. |
| 2009/0151717 | A1 | 6/2009 | Bowen et al. |
| 2013/0037041 | A1* | 2/2013 | Worm ................... A24F 47/008 131/329 |
| 2013/0068239 | A1 | 3/2013 | Youn |
| 2013/0081642 | A1 | 4/2013 | Safari |
| 2013/0152922 | A1 | 6/2013 | Benassayag et al. |
| 2013/0167854 | A1 | 7/2013 | Shin |
| 2013/0199528 | A1* | 8/2013 | Goodman ............. A24F 47/008 128/203.26 |
| 2013/0298905 | A1 | 11/2013 | Levin et al. |
| 2014/0041658 | A1 | 2/2014 | Goodman et al. |
| 2014/0096782 | A1 | 4/2014 | Ampolini et al. |
| 2014/0109921 | A1 | 4/2014 | Chen |
| 2014/0158129 | A1 | 6/2014 | Pratt, Jr. et al. |
| 2014/0224248 | A1 | 8/2014 | Edwards et al. |
| 2014/0253144 | A1 | 9/2014 | Novak, III et al. |
| 2014/0270727 | A1 | 9/2014 | Ampolini et al. |
| 2014/0283859 | A1 | 9/2014 | Minskoff et al. |
| 2014/0301721 | A1* | 10/2014 | Ruscio .................. A24F 47/008 392/386 |
| 2015/0040929 | A1 | 2/2015 | Hon |
| 2016/0128384 | A1* | 5/2016 | Luciani ................ A24F 47/008 131/329 |
| 2016/0135504 | A1* | 5/2016 | Li ......................... A24F 47/008 392/395 |
| 2016/0219934 | A1* | 8/2016 | Li ......................... A24F 47/008 |
| 2016/0270441 | A1 | 9/2016 | Lewis et al. |
| 2017/0006917 | A1 | 1/2017 | Alvarez |
| 2017/0143042 | A1* | 5/2017 | Batista ................. A24F 47/008 |
| 2017/0150753 | A1 | 6/2017 | Macko |
| 2018/0098570 | A1 | 4/2018 | Hon |
| 2018/0104214 | A1 | 4/2018 | Raichman |
| 2018/0206551 | A1 | 7/2018 | Liu |

FOREIGN PATENT DOCUMENTS

| | | |
|---|---|---|
| CN | 102892448 A | 1/2013 |
| CN | 103501847 A | 1/2014 |
| CN | 103929988 A | 7/2014 |
| CN | 104114050 A | 10/2014 |
| CN | 204104838 U | 1/2015 |
| CN | 204120222 U | 1/2015 |
| EP | 2617303 A1 | 7/2013 |
| WO | WO-2013/040193 A2 | 3/2013 |
| WO | WO-2014/195859 A2 | 12/2014 |
| WO | WO-2014207719 A1 | 12/2014 |

OTHER PUBLICATIONS

International Search Report and Written Opinion for Corresponding Application No. PCT/US2016/028039 dated Nov. 2, 2017.
Office Action for corresponding U.S. Appl. No. 15/239,304 dated Feb. 26, 2019.
Eurasian Notification dated Nov. 9, 2018 for corresponding Eurasian Application No. 201792326.
Office Action for corresponding U.S. Appl. No. 15/239,304 dated Aug. 21, 2019.
Office Action for corresponding Chinese Application No. 201680023593.0 dated Nov. 4, 2019.
Office Action for corresponding U.S. Appl. No. 15/239,304 dated Nov. 1, 2019.

* cited by examiner

100

E-VAPOR DEVICES INCLUDING PRE-SEALED CARTRIDGES

BACKGROUND

Field

The present disclosure relates to electronic vapor devices including self-contained articles including vapor precursors.

Description of Related Art

Some e-vapor devices include a first section coupled to a second section via a threaded connection. The first section may be a replaceable cartridge, and the second section may be a reusable fixture. The threaded connection may be a combination of a male threaded member on the first section and a female threaded receiver on the second section. The first section includes an outer tube (or housing) extending in a longitudinal direction and an inner tube within the outer tube. The inner tube may be coaxially positioned within the outer tube. The second section may also include the outer tube (or housing) extending in a longitudinal direction. The e-vapor device includes a central air passage defined in part by the inner tube and an upstream seal. Additionally, the e-vapor device includes a reservoir. The reservoir is configured to hold a vapor precursor and optionally a storage medium operable to store the vapor precursor therein. The reservoir is contained in an outer annulus between the outer tube and the inner tube. The outer annulus is sealed by the seal at an upstream end and by a stopper at a downstream end so as to prevent leakage of the vapor precursor from the reservoir.

SUMMARY

An e-vapor device may include a cartridge configured to hold a vapor precursor therein. The e-vapor device may additionally include a dispensing body including a ratchet assembly and configured to receive a vaporizer to interact with the ratchet assembly. The vaporizer is configured to access the vapor precursor in the cartridge via a coupling action and to heat the vapor precursor to generate a vapor. The ratchet assembly is configured to undergo a mechanical incrementation with each coupling action to facilitate a simultaneous removal of the cartridge with the vaporizer coupled thereto after a designated number of coupling actions.

The cartridge may be in a form of a mouthpiece. The cartridge may be a hermetically-sealed container. The cartridge may be sealed with a ball check valve arrangement.

The vaporizer may be configured to press against a ball structure of the ball check valve arrangement to release the vapor precursor within the cartridge during the coupling action. The vaporizer may be configured to unite with the cartridge via a snap-fit arrangement during the coupling action.

The ratchet assembly may be configured to rotate in response to the coupling action as part of the mechanical incrementation. The ratchet assembly may be configured to initially latch onto the vaporizer during the coupling action and to incrementally disengage from the vaporizer with each coupling action such that the vaporizer is released from the ratchet assembly after the designated number of coupling actions. Alternatively, the ratchet assembly may be configured to incrementally engage the vaporizer to the cartridge with each coupling action such that the vaporizer is conjoined to the cartridge after the designated number of coupling actions. The ratchet assembly may be configured to facilitate the simultaneous removal of the cartridge with the vaporizer coupled thereto after two to ten coupling actions (e.g., three to six coupling actions).

The e-vapor device may further include a mouthpiece structure configured to house the cartridge and to connect with the dispensing body such that the cartridge is between the mouthpiece structure and the dispensing body. An outer surface of the cartridge may be configured to conform to an inner surface of the mouthpiece structure. The cartridge may be integrated with the mouthpiece structure.

An e-vapor device may include a cartridge configured to hold a vapor precursor therein, the cartridge being a sealed container. The e-vapor device may additionally include a dispensing body including a mouthpiece end and a vaporizer at an opposing base end. The base end is configured to couple with the cartridge such that the vapor precursor is in fluidic communication with the vaporizer. The vaporizer is configured to heat the vapor precursor to generate a vapor.

The cartridge may be sealed with a ball check valve arrangement. The dispensing body may further include a battery between the mouthpiece end and the vaporizer.

An e-vapor device may include a cartridge including a plurality of compartments, each of the plurality of compartments configured to hold a vapor precursor therein. The e-vapor device may additionally include a dispensing body including a vaporizer. The cartridge may be rotatably-mounted on the dispensing body via the vaporizer. The cartridge is configured to rotate around the vaporizer such that one of the plurality of compartments is aligned so as to be in fluidic communication with the vaporizer.

The cartridge may be disk-shaped. The plurality of compartments are fluidically-isolated from each other. The vaporizer may be configured to remain stationary during a rotation of the cartridge.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
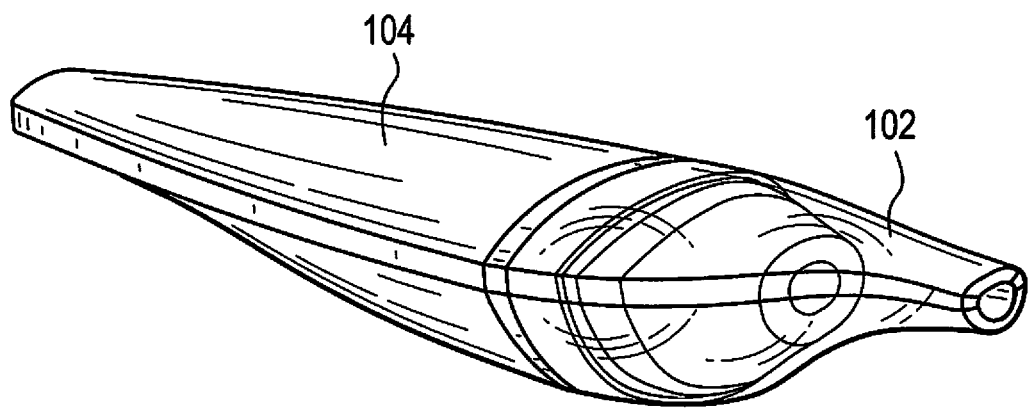
FIG. 1 is a perspective view of an e-vapor device with a mouthpiece/cartridge configuration according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a perspective view of an e-vapor device with a mouthpiece/cartridge configuration according to an example embodiment. Referring to FIG. 1, an e-vapor device 100 includes a mouthpiece structure 102 that is removably connected to a dispensing body 104. The mouthpiece structure 102 and the dispensing body 104 are shaped so as to provide a relatively smooth transition between their respective surfaces when joined together to form the e-vapor device 100. In an example embodiment, the e-vapor device 100 may have a flattened form so as to be wider than it is tall. Additionally, the dispensing body 104 may constitute a majority of the length of the e-vapor device 100. The back of the e-vapor device 100 (e.g., upper surface shown in FIG. 1) may be flatter than the underside of the e-vapor device 100. For instance, the underside of the e-vapor device 100 may have a belly that is fuller (e.g. more extended) at the adjoining portions of the mouthpiece structure 102 and the dispensing body 104 than at the end portions of the e-vapor device 100.

The mouthpiece structure 102 may include a cartridge that is configured to hold a vapor precursor (e.g., e-liquid) therein. A vapor precursor is a material or combination of materials that may be transformed into a vapor. For example, the vapor precursor may be a liquid, solid, and/or gel formulation including, but not limited to, water, beads, solvents, active ingredients, ethanol, plant extracts, natural or artificial flavors, and/or vapor formers such as glycerine and propylene glycol. The cartridge may be a hermetically-sealed container. The cartridge will be discussed in further detail in connection with subsequent figures. Inhalation of the vapor generated by the e-vapor device 100 occurs at the proximal end of the mouthpiece structure 102 (which is opposite to the end that is connected to the dispensing body 104). The mouthpiece structure 102 may taper toward the proximal end to form a snout-like configuration, which defines an outlet for the vapor. The dispensing body 104 may also taper toward the distal end (which is opposite to the end that is connected to the mouthpiece structure 102) to form a flattened tail-like structure. However, it should be understood that the mouthpiece structure 102, the dispensing body 104, and the overall e-vapor device 100 are not limited to the above examples and, thus, may have other suitable shapes, configurations, and forms (e.g., symmetrical shape).

The mouthpiece structure 102 may be integrated with the cartridge so as to engage with (and disengage from) the dispensing body 104 as a combined structure. In such an instance, the cartridge will not separate from the mouthpiece structure 102 during a normal operation of the e-vapor device 100. As a result, detaching the mouthpiece structure 102 from the dispensing body 104 will also result in the removal of the cartridge. Consequently, the mouthpiece structure 102 may be a single-use structure that is discarded with the cartridge (e.g., when replacing the cartridge).

Additionally, rather than a combined structure, the cartridge itself may be in a form of the mouthpiece structure 102 so as to be a single structure (instead of a plurality of integrated components) that is configured to be attached/detached from the dispensing body 104. The cartridge may be the mouthpiece structure 102, and the mouthpiece structure 102 may be the cartridge (instead of integrating a component that will function as the mouthpiece structure 102 with another component that will function as the cartridge to form a combined structure). In such an example, the internal volume of the mouthpiece structure 102 (other than the vapor passage extending therethrough) may contain the vapor precursor.

Alternatively, the mouthpiece structure 102 may be an independent component that houses the cartridge such that the cartridge may be separated from the mouthpiece structure 102 during a normal operation of the e-vapor device. For example, the cartridge may be configured to initially connect to the dispensing body 104 prior to connecting the mouthpiece structure 102 to the dispensing body 104 (and/or to the cartridge). The removal of the mouthpiece structure 102 and the cartridge may occur in the reverse order of their connection to the dispensing body 104. For instance, to replace the cartridge of the e-vapor device 100, the mouthpiece structure 102 may be initially detached from the dispensing body 104 to expose the cartridge, and then the cartridge may be detached from the dispensing body 104. After connecting the replacement cartridge to the dispensing body 104, the mouthpiece structure 102 may be reconnected to the dispensing body 104 so as to cover the cartridge.

Because the mouthpiece structure 102 may be configured as a permanent or semi-permanent component of the e-vapor device 100 and, thus, does not need to be discarded each time the cartridge is replaced, the mouthpiece structure 102 may be provided with aesthetic effects. Notably, the mouthpiece structure 102 may, in addition to its intended functionality, provide a visual or other sensory appeal to the adult vaper. In particular, the mouthpiece structure 102 may be formed of an ornamental material (e.g., wood, metal, ceramic, plastic) and/or include designs (e.g., patterns, images, characters). Thus, the mouthpiece structure 102 may be customized so as to provide an expression of personality and individuality by an adult vaper.

The dispensing body 104 may include a ratchet assembly and is configured to receive a vaporizer to interact with the ratchet assembly. The ratchet assembly will be discussed in further detail in connection with subsequent figures. The vaporizer is configured to access the vapor precursor in the cartridge via a coupling action and to heat the vapor precursor to generate a vapor. In an example embodiment, the ratchet assembly is configured to undergo a mechanical incrementation with each coupling action (between the vaporizer and the cartridge) to facilitate a simultaneous removal of the cartridge with the vaporizer coupled thereto after a designated number of coupling actions. As a result, the potential for overuse of the vaporizer (and the adverse sensory effects stemming therefrom) can be reduced or prevented.

Figure 2:
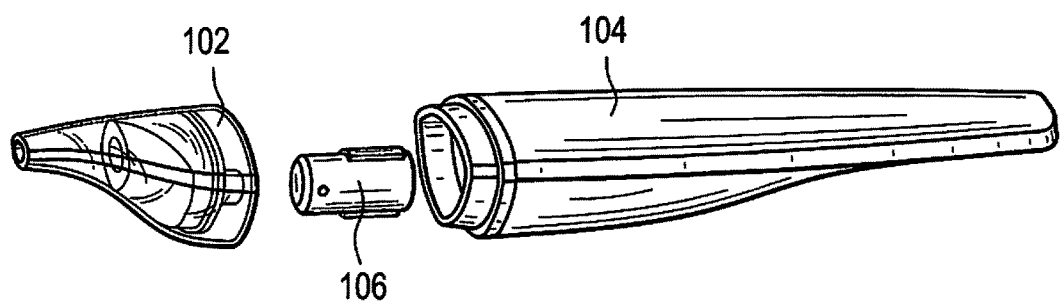
FIG. 2 is a partially exploded view of the e-vapor device of FIG. 1.

FIG. 2 is a partially exploded view of the e-vapor device of FIG. 1. Referring to FIG. 2, the dispensing body 104 is configured to receive a vaporizer 106. The vaporizer 106 may be cylindrically shaped with one or more guide structures on its outer side wall. The one or more guide structures may be in the form of one or more parallel ridges that extend along a partial length of the vaporizer 106. For instance, the ridges may be in the form of two parallel strips on opposite sides of the vaporizer 106, wherein the strips extend longitudinally from an end of the vaporizer 106 (that will be received by the dispensing body 104) along a partial length of the vaporizer 106 (e.g., along one-third to two-thirds a length of the vaporizer 106), although example embodiments are not limited thereto. When assembled, the mouthpiece structure 102 is configured to engage the concave end of the vaporizer 106 as well as the dispensing body 104.

Figure 3:
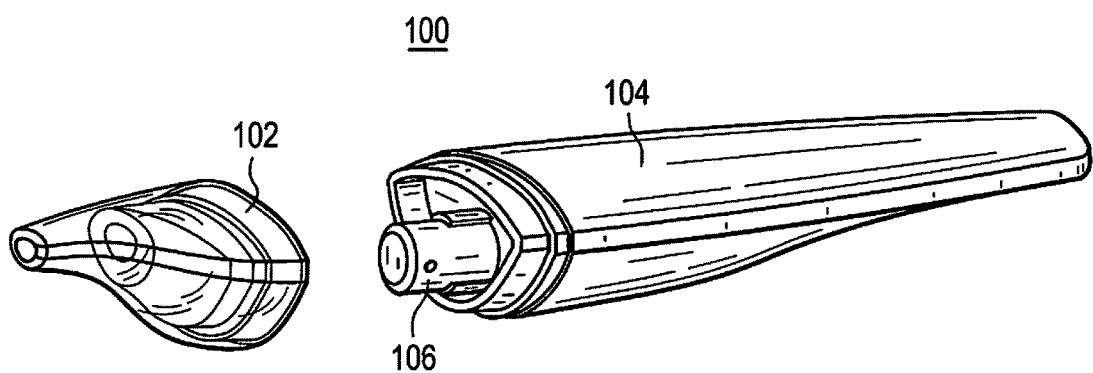
FIG. 3 is another partially exploded view of the e-vapor device of FIG. 1.

FIG. 3 is another partially exploded view of the e-vapor device of FIG. 1. Referring to FIG. 3, the dispensing body 104 includes a recess configured to accommodate the cylindrical shape of the vaporizer 106 and the guide structures on the outer side wall thereof so as to interact with a ratchet assembly within the dispensing body 104. The depth of the recess is such that the vaporizer 106 protrudes therefrom when in a neutral, resting position in the recess. In an example embodiment, the guide structures on the outer side wall of the vaporizer 106 also protrude from the recess when the vaporizer 106 is at equilibrium therein (e.g., in the absence of an external force pushing the vaporizer 106 into the recess). Because at least the surface defining the opening to the recess may be contoured to correspond to the circular cross-section of the vaporizer 106 and the guide structures on the outer side wall thereof, the vaporizer 106 may remain aligned in the recess and, thus, prevented from rotating therein while the guide structures overlap with the surface defining the opening to the recess. On the other hand, below the surface defining the opening to the recess, the volume of the recess may have a cylindrical shape that is larger than the cylindrical shape of the vaporizer 106 in order to accommodate the guide structures on the outer side wall thereof. As a result, the vaporizer 106 will be able to rotate if the vaporizer 106 is pushed into the dispensing body 104 such that the guide structures no longer overlap with the surface defining the opening to the recess.

Alternatively, the volume of the recess (in addition to the surface defining the opening thereto) may also correspond to the cylindrical shape of the vaporizer 106 and the guide structures on the outer side wall thereof such that the vaporizer 106 will remained aligned and, thus, unable to rotate while in the recess (regardless of whether an external force is applied to push vaporizer 106 into the dispensing body 104 such that the guide structures are below the surface defining the opening to the recess). However, it should be understood that example embodiments are not limited to the above, and other suitable configurations are possible depending on the intended interaction between the vaporizer 106 and the dispensing body 104 and/or the ratchet assembly (which will be discussed in further detail below).

Figure 4:
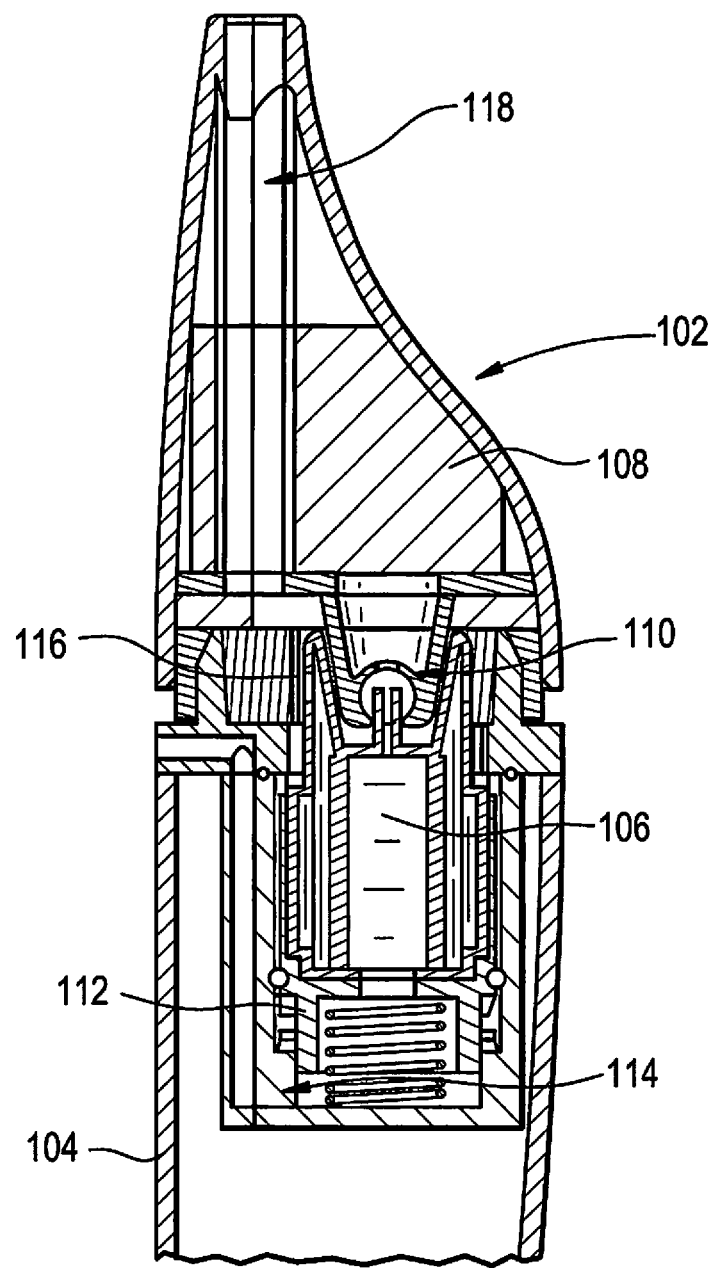
FIG. 4 is a partial, cross-sectional view of the e-vapor device of FIG. 1.

FIG. 4 is a partial, cross-sectional view of the e-vapor device of FIG. 1. Referring to FIG. 4, the mouthpiece structure 102 is configured to house the cartridge 108 and to connect with the dispensing body 104 such that the cartridge 108 is between the mouthpiece structure 102 and the dispensing body 104. An outer surface of the cartridge 108 may be configured to conform to an inner surface of the mouthpiece structure 102. The mouthpiece structure 102 and the cartridge 108 may be configured as two independent components that are designed to be separated during a normal operation of the e-vapor device 100. In such an instance, the mouthpiece structure 102 may be reusable, while the cartridge 108 may be disposable.

Alternatively, the mouthpiece structure 102 and the cartridge 108 may be integrated so as to form a single, combined structure that is not designed to be separated during a normal operation of the e-vapor device 100. In such an instance, the combined mouthpiece structure 102 and cartridge 108 may be disposable. Furthermore, the cartridge 108 itself may be in the form of the mouthpiece structure 102 (and vice versa) such that an internal volume therein (other than the vapor passage 118) may be filled with the vapor precursor.

The cartridge 108 may connect with the vaporizer 106 via a number of possible configurations. Additionally, the mouthpiece structure 102 may engage with the dispensing body 104 to fortify the connection between the cartridge 108 and the vaporizer 106. Suitable attachment structures that may be provided on the applicable surfaces of the e-vapor device 100 to be joined include mating member/recess type arrangements and magnetic arrangements, although example embodiments are not limited thereto.

For instance, the attachment structure may include a mating member that is formed on a first surface of the e-vapor device 100 and a corresponding recess that is formed on a second surface of the e-vapor device 100. In a non-limiting embodiment, the mating member may be a rounded structure to facilitate the engagement/disengagement of the attachment structure, while the recess may be a concave indentation that corresponds to the curvature of the rounded structure. The mating member may also be spring-loaded so as to retract (via spring compression) during an initial insertion and to protract (via spring decompression) when mating member becomes aligned with the corresponding recess. The engagement of the mating member with the corresponding recess may result in an audible click, which notifies the adult vaper of a proper connection.

In another example, the attachment structure may include a magnetic arrangement. For instance, a first magnet may be arranged in a first surface of the e-vapor device 100 and a second magnet may be arranged in a second surface of the e-vapor device 100. The first and/or second magnets may be exposed or hidden from view behind a layer of material. The first and second magnets are oriented so as to be attracted to each other, and a plurality of pairs of the first and second magnets may be provided to ensure a proper connection between the desired surfaces.

In an example embodiment, the cartridge 108 may be structured to have a lower protruding portion (that is opposite the end adjacent to the vapor outlet of the mouthpiece structure 102) that is configured to engage with the concave end of the vaporizer 106. The cartridge 108 may be configured to unite with the vaporizer 106 via a friction-fit arrangement or a snap-fit arrangement, although example embodiments are not limited thereto. In addition, a coupling action may occur so that the vaporizer 106 can access (e.g., be in fluidic communication with) the vapor precursor in the cartridge 108. The coupling action may occur simultaneously with or subsequent to the connection of the cartridge 108 to the vaporizer 106.

Access to the vapor precursor in the cartridge 108 is restricted by a seal 110. The seal 110 may be in a form of a ball check valve arrangement. In such an instance, the vaporizer 106 may include an access member that is configured to press against a ball structure of the ball check valve arrangement to release the vapor precursor within the cartridge 108 during the coupling action. The access member of the vaporizer 106 may draw the vapor precursor (e.g., via capillary action) from the cartridge 108 into the vaporizer 106. Because the ball structure of the ball check valve arrangement is spring-biased, the ball structure will press against an inner surface of the outlet of the cartridge 108 to reseal the cartridge 108 when the cartridge 108 is detached from the vaporizer 106 (e.g., during replacement of the cartridge 108). In another example, the seal 110 may be an impermeable material that is designed to be pierced by the access member of the vaporizer 106 in order to access the vapor precursor within the cartridge 108.

The coupling action may involve pressing the mouthpiece structure 102 against the dispensing body 104 to obtain the proper connection. In particular, the cartridge 108 may be pushed against the corresponding portion of the vaporizer 106 to establish the requisite fluidic communication therebetween. During the operation of the e-vapor device 100, air may enter via an inlet 114 and exit via an outlet 116. The vapor may be dispensed via the vapor passage 118. The force applied to achieve the coupling action may result in a temporary, longitudinal displacement of the vaporizer 106. The vaporizer 106 interacts with the ratchet assembly 112 in the dispensing body 104, and a spring may be arranged under the ratchet assembly 112. The ratchet assembly 112 may include a toothed structure and a pawl configured to engage the teeth of the toothed structure so as to permit only a one-way advancement (e.g., one direction of movement) of the toothed structure.

As noted above, the ratchet assembly 112 may be configured to undergo a mechanical incrementation with each coupling action between the cartridge 108 and the vaporizer 106. In particular, when a new cartridge 108 is loaded in the e-vapor device 100 by pushing the new cartridge 108 against the corresponding portion of the vaporizer 106 to perform the coupling action, the force from the pushing will additionally cause the vaporizer 106 and the ratchet assembly 112 to undergo a temporary, longitudinal displacement into the dispensing body 104 via the spring while also causing the ratchet assembly to mechanically advance. For example, the ratchet assembly 112 may be configured to rotate in response to the coupling action as part of the mechanical incrementation. With the mechanical incrementation, the ratchet assembly 112 is configured to initially engage and hold the vaporizer 106 and to subsequently release the vaporizer 106 for simultaneous removal with the cartridge 108 after a designated number of mechanical incrementations.

In an example embodiment, the ratchet assembly 112 may be configured to initially latch onto the vaporizer 106 during the coupling action and to incrementally disengage from the vaporizer 106 with each coupling action such that the vaporizer 106 is released from the ratchet assembly 112 after the designated number of coupling actions. In particular, the ratchet assembly 112 may include a rim structure that is configured to rotate and obstruct the guide structures on the outer side wall of the vaporizer 106 when the vaporizer 106 undergoes a temporary, longitudinal displacement into the dispensing body 104 during a coupling action. As a result, the cartridge 108, when spent, will be detached from the e-vapor device 100 without also removing the vaporizer 106. The rim structure of the ratchet assembly 112 may be configured to rotate with each coupling action (e.g., insertion of a new cartridge 108) until a notched section (or similar arrangement) is reached that corresponds to each guide structure of the vaporizer 106, which will allow the guides structures to pass through via the notched sections, thereby releasing the vaporizer 106 for removal with the cartridge 108. Accordingly, the vaporizer 106 can be discarded after utilization with a designated number of cartridges 108, thus reducing or preventing the overuse of the vaporizer 106 and the potentially unpleasant sensory effects associated therewith.

Alternatively, the ratchet assembly 112 may be configured to incrementally engage the vaporizer 106 to the cartridge 108 with each coupling action such that the vaporizer 106 is conjoined to the cartridge 108 after the designated number of coupling actions. In such an instance, the cartridge 108 may be fluidically connected to the vaporizer 106 during the coupling action without establishing a mechanical connection therebetween that would be sufficient to allow the cartridge 108 and the vaporizer 106 to be simultaneously removed. Instead, the ratchet assembly 112 can be configured to establish such a mechanical connection after a designated number of coupling actions.

Figure 5:
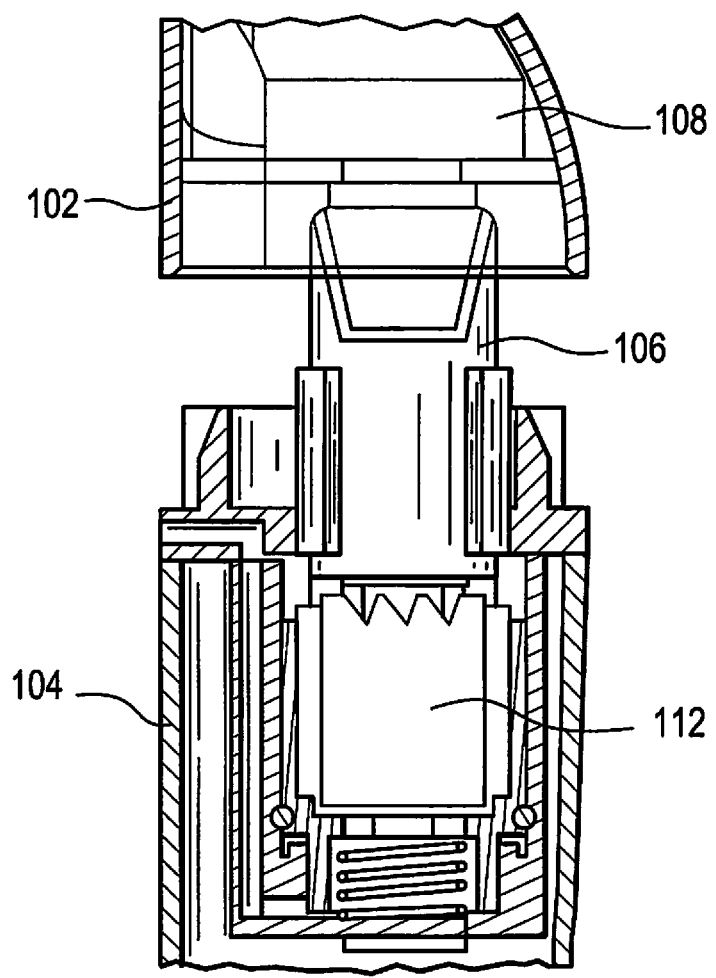
FIG. 5 is a partial, cross-sectional view of a simultaneous removal of the cartridge and vaporizer of the e-vapor device of FIG. 1.

FIG. 5 is a partial, cross-sectional view of a simultaneous removal of the cartridge and vaporizer of the e-vapor device of FIG. 1. Referring to FIG. 5, the ratchet assembly 112 may be configured to facilitate the simultaneous removal of the cartridge 108 with the vaporizer 106 coupled thereto after two to ten coupling actions (e.g., three to six coupling actions or four to five coupling actions). In an example embodiment, each coupling action may correspond to the connection of a new cartridge 108 to the vaporizer 106. For instance, the e-vapor device 100 may be configured such that an adult vaper may replace the cartridge 108 three times, and upon depletion of the third replacement cartridge 108, the vaporizer 106 may be pulled out together with the depleted third replacement cartridge 108 and discarded. The frequency of replacement for the vaporizer 106 may depend on the vapor precursor of the cartridge 108 and/or operating parameters of the e-vapor device 100.

Figure 6:
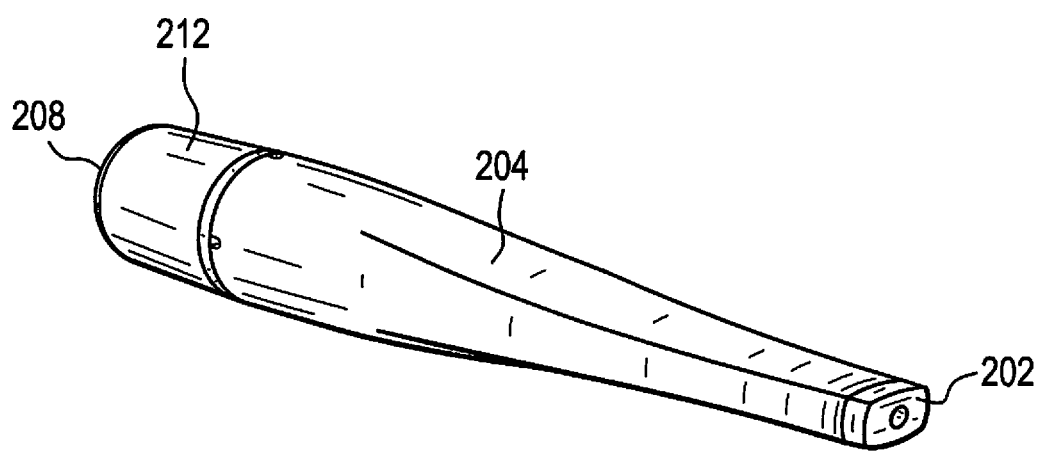
FIG. 6 is a perspective view of an e-vapor device with a cartridge-in-base configuration according to an example embodiment.

FIG. 6 is a perspective view of an e-vapor device with a cartridge-in-base configuration according to an example embodiment. Referring to FIG. 6, the e-vapor device 200 includes a base structure 212 that is connected to a dispensing body 204. The dispensing body 204 includes a mouthpiece end with a mouthpiece structure 202 and a vaporizer at an opposing base end. The base end is configured to couple with a cartridge 208 such that a vapor precursor is in fluidic communication with the vaporizer. The cartridge 208 is configured to hold the vapor precursor therein. The cartridge 208 may be a sealed container. The vaporizer is configured to heat the vapor precursor to generate a vapor.

Figure 7:
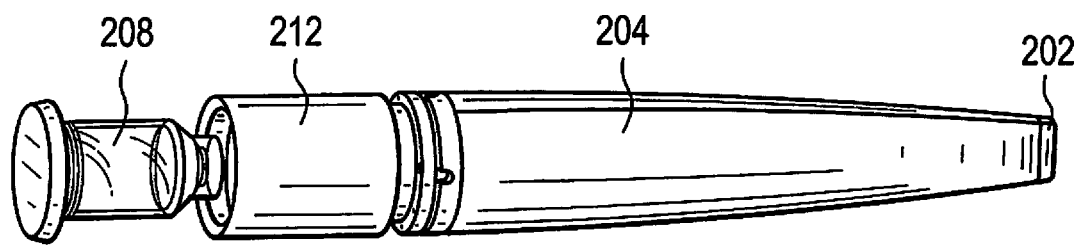
FIG. 7 is a partially exploded view of the e-vapor device of FIG. 6.

FIG. 7 is a partially exploded view of the e-vapor device of FIG. 6. Referring to FIG. 7, the dispensing body 204 may taper toward the mouthpiece structure 202. The base structure 212 may be attached to the dispensing body 204 via a threaded arrangement, although example embodiments are not limited thereto. The cartridge 208 is configured for insertion into the base structure 212 and may be secured via a number of suitable arrangements.

Figure 8:
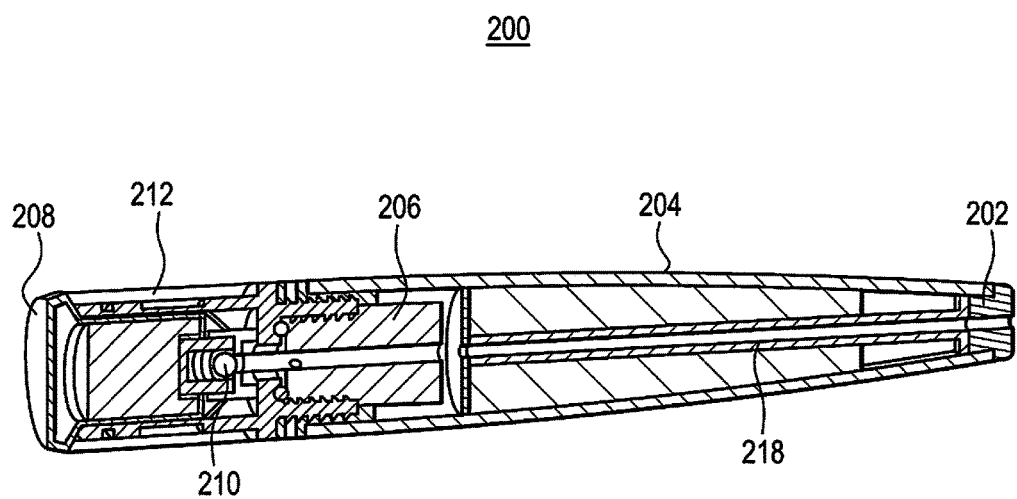
FIG. 8 is a cross-sectional view of the e-vapor device of FIG. 6.

FIG. 8 is a cross-sectional view of the e-vapor device of FIG. 6. Referring to FIG. 8, access to the vapor precursor in the cartridge 208 may be restricted with a seal 210. The seal 210 may be a ball check valve arrangement, although example embodiments are not limited thereto. The vaporizer 206 is arranged within the base end of the dispensing body 204. A vapor passage 218 extends within the dispensing body 204 from the vaporizer 206 to the mouthpiece structure 202. The dispensing body 204 may further include a battery between the mouthpiece structure 202 at the mouthpiece end and the vaporizer 206 at the opposing base end.

Figure 9:
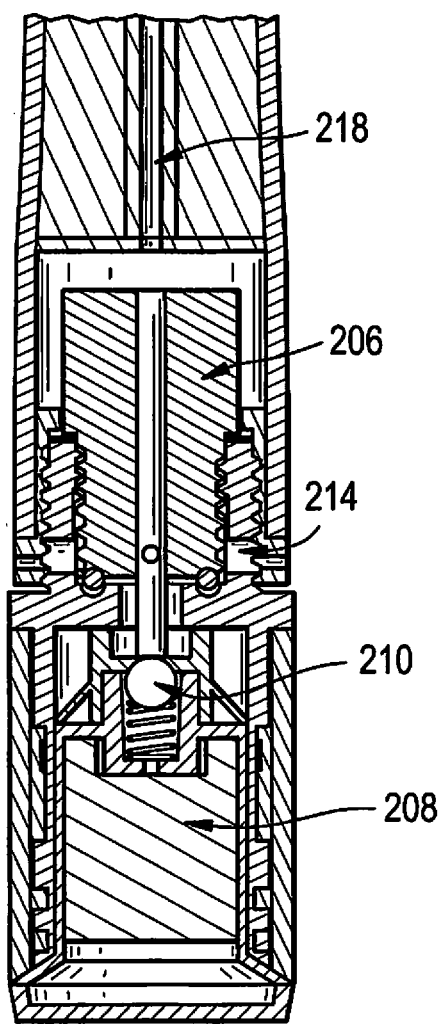
FIG. 9 is a partial, cross-sectional view of the e-vapor device of FIG. 6.

FIG. 9 is a partial, cross-sectional view of the e-vapor device of FIG. 6. Referring to FIG. 9, the ball structure of the ball check valve arrangement of the seal 210 is pushed inward when the cartridge 208 is coupled to the vaporizer 206, thereby allowing the vapor precursor in the cartridge 208 to be in fluidic communication with the vaporizer 206. Air may flow into the vaporizer 206 via an inlet 214. The vapor generated by the vaporizer 206 is directed through the vapor passage 218 to the mouthpiece structure 202.

Figure 10:
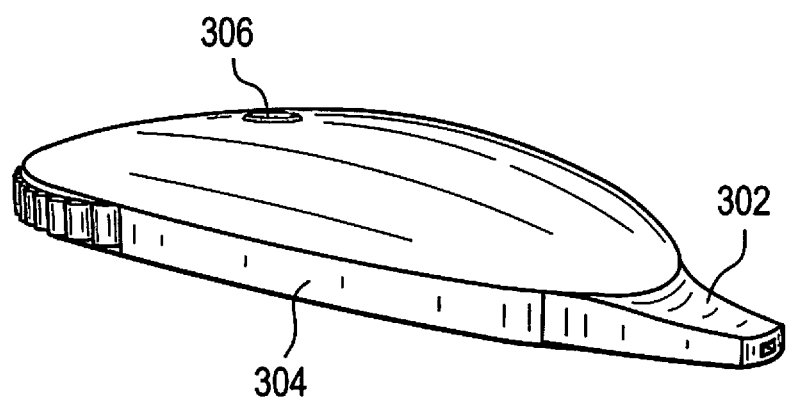
FIG. 10 is a perspective view of an e-vapor device with a disk cartridge configuration according to an example embodiment.

FIG. 10 is a perspective view of an e-vapor device with a disk cartridge configuration according to an example embodiment. Referring to FIG. 10, the e-vapor device 300 includes a dispensing body 304 having a disk-like shape. The mouthpiece structure 302 is connected to a side surface of the dispensing body 304. The vaporizer 306 is visible through a top surface of the dispensing body 304.

Figure 11:
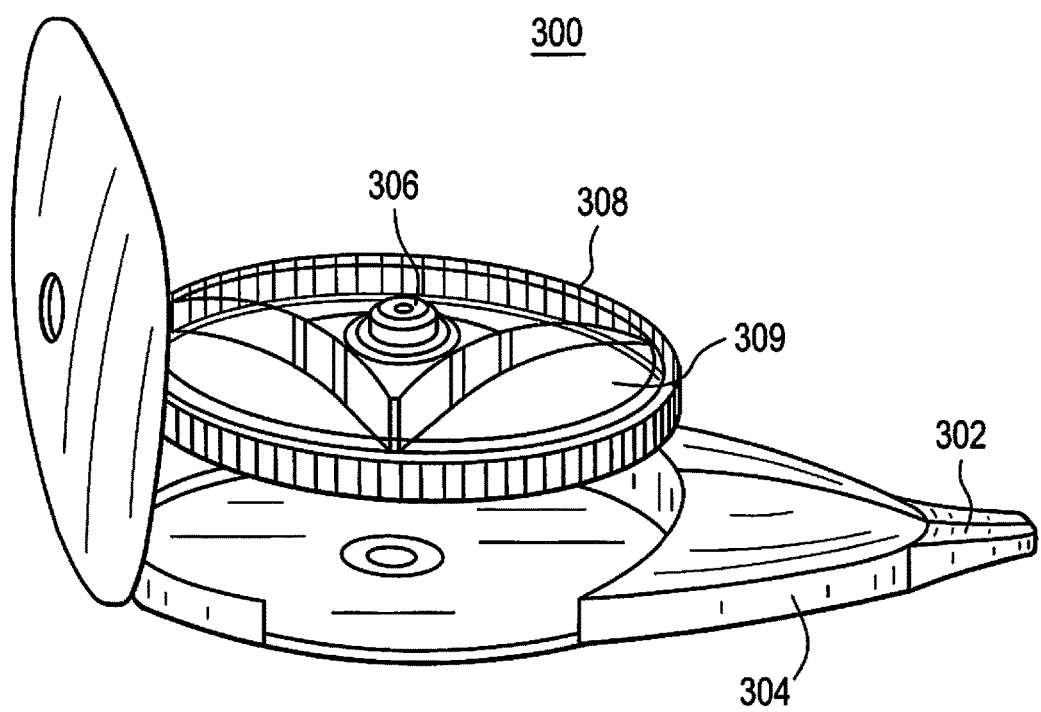
FIG. 11 is a partially exploded view of the e-vapor device of FIG. 10.

FIG. 11 is a partially exploded view of the e-vapor device of FIG. 10. Referring to FIG. 11, the dispensing body 304 includes a pivotable lid structure that is configured to open/close to receive (or remove) a cartridge 308 having a disk shape. The cartridge 308 includes a plurality of compartments 309. Although three compartments 309 are shown in FIG. 11, it should be understood that example embodiments are not limited thereto. For instance, the cartridge 308 may include two, four, or more compartments 309. Each of the plurality of compartments 309 is configured to hold a vapor precursor therein. In addition, the plurality of compartments 309 are fluidically-isolated from each other. As a result, each compartment 309 of the cartridge 308 may hold a vapor precursor of a different flavor and/or composition.

The vaporizer 306 may be structured to be a part of the dispensing body 304 or the cartridge 308. When the vaporizer 306 is structured to be a part of the dispensing body 304, the cartridge 308 may be structured to have an opening that is configured to engage the vaporizer 306. On the other hand, when the vaporizer 306 is structured to be a part of the cartridge 308, the dispensing body 304 may be configured to allow an engagement with the vaporizer 306. The cartridge 308 may be rotatably-mounted on the dispensing body 304 via the vaporizer 306. The cartridge 308 is configured to rotate around the vaporizer 306 such that one of the plurality of compartments 309 is aligned so as to be in fluidic communication with the vaporizer 306.

Figure 12:
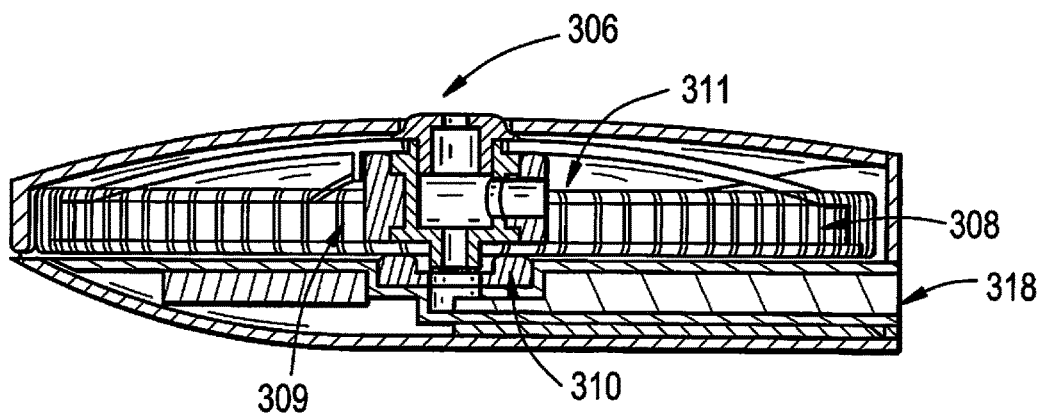
FIG. 12 is a partial, cross-sectional view of the e-vapor device of FIG. 10.

FIG. 12 is a partial, cross-sectional view of the e-vapor device of FIG. 10. Referring to FIG. 12, the vaporizer 306 is configured to remain stationary during a rotation of the cartridge 308. The feed tube 311 also remains stationary with the vaporizer 306. Each of the plurality of compartments 309 includes an outlet that is configured to align with the feed tube 311 upon rotation of the cartridge 308. Various arrangements may be used to help ensure a proper alignment of the feed tube 311 with the outlet of a desired one of the plurality of compartments 309 (e.g., mating member/recess type arrangements, magnetic arrangements). A seal 310 may be provided between vaporizer 306 and the vapor passage 318. During an operation of the e-vapor device 300, air may enter the vaporizer 306 from an opening in its top surface. The vapor generated by the vaporizer 306 is directed through the vapor passage 318 to the mouthpiece structure 302.

The e-vapor devices disclosed herein may be provided with memory devices and the associated circuitry so as to allow the receipt, storage, and transmission of information to/from other electronic devices. The smart capability, connecting features, and other related aspects of the mouthpiece structure, cartridge, dispensing body, and overall e-vapor device are additionally discussed in U.S. Application No. 62/151,148 (now U.S. application Ser. No. 14/998,020), U.S. Application No. 62/151,160, and U.S. Application No. 62/151,179, the entire contents of each of which are incorporated herein by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An e-vapor device comprising:
a cartridge configured to hold a vapor precursor therein; and
a dispensing body including a ratchet assembly and configured to receive a vaporizer to interact with the ratchet assembly, the vaporizer configured to fluidically access the vapor precursor in the cartridge via a coupling action and to heat the vapor precursor to generate a vapor, the cartridge configured such that the vapor precursor therein is not in fluidic communication with the vaporizer prior to the coupling action, the ratchet assembly configured to undergo a mechanical incrementation with each coupling action to facilitate a simultaneous removal of the cartridge with the vaporizer coupled thereto after a designated number of coupling actions, the ratchet assembly configured to incrementally engage the vaporizer to the cartridge with each coupling action such that the vaporizer is conjoined to the cartridge after the designated number of coupling actions, the cartridge having a lower protruding portion, the vaporizer having a concave end, the lower protruding portion of the cartridge configured to engage with the concave end of the vaporizer during the coupling action.

2. The e-vapor device of claim 1, wherein the cartridge is in a form of a mouthpiece.

3. The e-vapor device of claim 1, wherein the cartridge is a hermetically-sealed container.

4. The e-vapor device of claim 1, wherein the cartridge is sealed with a ball check valve arrangement.

5. The e-vapor device of claim 4, wherein the vaporizer is configured to press against a ball structure of the ball check valve arrangement to release the vapor precursor within the cartridge during the coupling action.

6. The e-vapor device of claim 1, wherein the vaporizer is configured to unite with the cartridge via a snap-fit arrangement during the coupling action.

7. The e-vapor device of claim 1, wherein the ratchet assembly is configured to rotate in response to the coupling action as part of the mechanical incrementation.

8. The e-vapor device of claim 1, wherein the ratchet assembly is configured to initially latch onto the vaporizer during the coupling action and to incrementally disengage from the vaporizer with each coupling action such that the vaporizer is released from the ratchet assembly after the designated number of coupling actions.

9. The e-vapor device of claim 1, further comprising:
a mouthpiece structure configured to house the cartridge and to connect with the dispensing body such that the cartridge is between the mouthpiece structure and the dispensing body.

10. The e-vapor device of claim 9, wherein an outer surface of the cartridge is configured to conform to an inner surface of the mouthpiece structure.

11. The e-vapor device of claim 9, wherein the cartridge is integrated with the mouthpiece structure.

12. The e-vapor device of claim 1, wherein the vaporizer is configured to be received by the dispensing body prior to the coupling action with the cartridge.

13. The e-vapor device of claim 1, wherein the cartridge and the vaporizer are separate structures that are not united until the coupling action.

14. An e-vapor device comprising:
a cartridge configured to hold a vapor precursor therein; and
a dispensing body including a ratchet assembly and configured to receive a vaporizer to interact with the ratchet assembly, the vaporizer configured to fluidically access the vapor precursor in the cartridge via a coupling action and to heat the vapor precursor to generate a vapor, the cartridge configured such that the vapor precursor therein is not in fluidic communication with the vaporizer prior to the coupling action, the ratchet assembly configured to undergo a mechanical incrementation with each coupling action to facilitate a simultaneous removal of the cartridge with the vaporizer coupled thereto after a designated number of coupling actions, the ratchet assembly configured to facilitate the simultaneous removal of the cartridge with the vaporizer coupled thereto after two to ten coupling actions, the cartridge having a lower protruding portion, the vaporizer having a concave end, the lower protruding portion of the cartridge configured to engage with the concave end of the vaporizer during the coupling action.

* * * * *